(12) United States Patent
Iversen et al.

(10) Patent No.: US 11,883,388 B2
(45) Date of Patent: Jan. 30, 2024

(54) METHODS AND COMPOSITIONS TO INHIBIT SYMPTOMS ASSOCIATED WITH VIRAL UPPER RESPIRATORY TRACT INFECTIONS

(71) Applicant: SEN-JAM Pharmaceutical Inc., Huntington, NY (US)

(72) Inventors: Jacqueline M. Iversen, Lloyd Harbor, NY (US); Thomas A. Dahl, Guilford, CT (US)

(73) Assignee: SEN-JAM Pharmaceutical Inc., Huntington, NY (US)

( * ) Notice: Subject to any disclaimer, the term of this patent is extended or adjusted under 35 U.S.C. 154(b) by 29 days.

(21) Appl. No.: 16/897,849

(22) Filed: Jun. 10, 2020

(65) Prior Publication Data

US 2020/0297707 A1    Sep. 24, 2020

Related U.S. Application Data

(63) Continuation of application No. 16/009,751, filed on Jun. 15, 2018, now abandoned.

(60) Provisional application No. 62/520,857, filed on Jun. 16, 2017.

(51) Int. Cl.
| | |
|---|---|
| *A61K 31/445* | (2006.01) |
| *A61P 11/00* | (2006.01) |
| *A61K 31/192* | (2006.01) |
| *A61K 31/4545* | (2006.01) |
| *A61K 31/616* | (2006.01) |
| *A61K 31/4535* | (2006.01) |
| *A61K 9/00* | (2006.01) |
| *A61K 9/68* | (2006.01) |
| *A61K 9/20* | (2006.01) |

(52) U.S. Cl.
CPC .......... *A61K 31/445* (2013.01); *A61K 9/0056* (2013.01); *A61K 9/0058* (2013.01); *A61K 9/2004* (2013.01); *A61K 31/192* (2013.01); *A61K 31/4535* (2013.01); *A61K 31/4545* (2013.01); *A61K 31/616* (2013.01); *A61P 11/00* (2018.01)

(58) Field of Classification Search
CPC .. A61K 31/445; A61K 9/0056; A61K 9/0058; A61K 9/2004; A61K 31/192; A61K 31/4535; A61K 31/4545; A61K 31/616; A61K 2300/00; A61P 11/00
See application file for complete search history.

(56) References Cited

U.S. PATENT DOCUMENTS

| | | | | |
|---|---|---|---|---|
| 5,373,022 | A * | 12/1994 | Fawzi | A61P 25/04 |
| | | | | 514/570 |
| 10,420,756 | B2 | 9/2019 | Iversen et al. | |
| 10,675,261 | B2 | 6/2020 | Iversen et al. | |
| 10,765,630 | B2 | 9/2020 | Iversen et al. | |
| 10,874,653 | B2 | 12/2020 | Iversen et al. | |
| 11,129,803 | B2 | 9/2021 | Iversen et al. | |
| 11,464,766 | B2 | 10/2022 | Iversen et al. | |
| 2004/0253311 | A1* | 12/2004 | Berlin | A61P 43/00 |
| | | | | 514/217.05 |
| 2005/0266032 | A1* | 12/2005 | Srinivasan | A61K 45/06 |
| | | | | 514/649 |

* cited by examiner

*Primary Examiner* — Theodore R. Howell

(74) *Attorney, Agent, or Firm* — Morgan, Lewis & Bockius LLP

(57) ABSTRACT

The present invention relates to a method of reducing or preventing the symptoms associated with the common cold. The method comprises administering to a subject an effective amount of a pharmaceutical composition before presenting with at least one symptom of the common cold. The pharmaceutical composition comprises a non-steroidal anti-inflammatory drug and a co-agent selected from the group consisting of: fexofenadine, ketotifen, desloratadine, salts thereof, and combinations thereof.

14 Claims, No Drawings

METHODS AND COMPOSITIONS TO INHIBIT SYMPTOMS ASSOCIATED WITH VIRAL UPPER RESPIRATORY TRACT INFECTIONS

This application is a continuation application of U.S. patent application Ser. No. 16/009,751, filed on Jun. 15, 2018, which claims the benefit of U.S. Provisional Application Ser. No. 62/520,857, filed Jun. 16, 2017, the disclosures of the aforementioned applications are incorporated herein by reference in their entireties.

FIELD OF THE INVENTION

The present invention relates to methods, and compositions, for inhibiting the acute symptoms associated with a viral upper respiratory tract infection (i.e., acute viral rhinitis, viral nasopharyngitis, rhinopharyngitis, acute coryza), colloquially known as the common cold.

BACKGROUND OF THE INVENTION

The common cold is an acute, self-limiting viral infection of the upper respiratory tract involving the nose, sinuses, pharynx and larynx. Over two hundred virus strains are implicated in the cause of the common cold; the rhinoviruses are the most common. The virus is spread by hand contact with secretions from an infected person (direct or indirect) or aerosol of the secretions and virus. The incubation period varies but is about two days for rhinovirus.

Symptoms, which generally relate to the infected mucosa, typically peak at 1-3 days and last 7-10 days. Some symptoms may last up to three weeks (Heikkinen et al., "The common cold", *Lancet* (2003) 361(9351):51-9). Symptoms may last longer in people who smoke. Symptoms include sore throat, rhinitis, rhinorrhea, cough, malaise, runny nose, sneezing, headache, and fever. The severity and type of symptoms will vary among individuals and with different infective agents. For example, fever is common in children but rare and mild in adults.

Children under two years have about six infections a year, adults have about two to three infections a year, and older people have about one infection per year. Stress and poor sleep may increase the risk of the common cold among adults; whereas attendance at a daycare center increases the risk among preschool children.

Although self-limiting, the common cold is highly prevalent and its symptoms may be debilitating. The symptoms cause decline in function and productivity at work (Smith et al., "Effects of upper respiratory tract illnesses on mood and performance over the working day," *Ergonomics* (2000) 43:752-63; Bramley et al., "Productivity losses related to the common cold." *J Occup Environ Med* (2002) 44:822-9) and may affect other activities such as driving (Smith et al., "An investigation of the effects of the common cold on simulated driving performance and detection of collisions: a laboratory study," *BMJ Open* (2012); 2:pii:e001047). The impact of the common cold on society and health care is large. Of individuals with an upper respiratory tract infection, 7%-17% of adults and 33% of children visit a physician for alleviation of symptoms. The common cold results in an estimated increase of 12.5% in patient visits per month during cold and flu season (Sauro et al., "Do influenza and acute respiratory infective diseases weigh heavily on general practitioners' daily practice?" *Eur J Gen Pract* (2006) 12:34-6). In the United States, direct medical costs related to the common cold (e.g., physician visits, secondary infections and medications) were an estimated $17 billion a year in 1997 (Fendrick et al., "The economic burden of non-influenza-related viral respiratory tract infection in the United States," *Arch Intern Med* (2003); 163:487-94). Indirect costs due to missed work because of illness or caring for an ill child were an estimated $25 billion a year.

There is no vaccine or cure for the common cold. The primary methods of prevention are physical interventions, such as, hand washing; not touching the eyes, nose or mouth with unwashed hands; and perhaps gargling. Other modes of prevention have been proposed with varying results. For instance, zinc appears to be effective in reducing the number of colds per year in children. However, the proposed use of probiotics, vitamin C and ginseng has produced inconsistent results. (Allan et al., "Prevention and treatment of the common cold: making sense of the evidence," *CMAJ* (2014) 186(3):190-199.) Due to the lack of an effective manner of prevention, the symptoms of the common cold have only been treated once they appear.

Clearly, there is a need for a more effective and accessible manner by which to manage the symptoms of the common cold.

SUMMARY OF THE INVENTION

In one aspect, the present invention provides a method of inhibiting the symptoms associated with the common cold, the method comprising administering to a subject, in need thereof, an effective amount of a pharmaceutical composition prior to the appearance of at least one symptom of the common cold. Typically, the pharmaceutical composition is administered daily before the appearance of a symptom, e.g., at most about a week before the appearance, or at most about three days before the appearance, or at least about two days before the appearance, or at least about one day before the appearance, or at least about 12 hours before the appearance, or at least about six hours before the appearance, or at least about three hours before the appearance, or at least about one hour before the appearance, or right before the appearance.

In another aspect, the present invention provides a method of inhibiting the symptoms associated with the common cold, the method comprising administering to a subject, in need thereof, an effective amount of a pharmaceutical composition at the first appearance of at least one symptom of the common cold, or within about 12 hours of the first appearance of at least one symptom, or within about 24 hours of the first appearance of at least one symptom.

The pharmaceutical composition comprises a) a non-steroidal anti-inflammatory drug (NSAID), and/or a salt thereof; and b) a co-agent selected from the group consisting of fexofenadine, ketotifen, desloratadine, salts thereof, and combinations thereof.

Typically, the NSAID is aspirin, ibuprofen, naproxen, diclofenac, diflunisal, etodolac, indomethacin, ketoprofen, ketorolac, meloxicam, nabumetone, oxaprozin, piroxicam, salsalate, sulindac, tolmetin or combinations thereof.

In a preferred embodiment, the non-steroidal anti-inflammatory drug is naproxen sodium and the co-agent is fexofenadine. In one embodiment, the amount of naproxen sodium is about 220 mg to about 880 mg, and the amount of fexofenadine is about 60 mg to about 180 mg. In one embodiment, the naproxen sodium and the fexofenadine is combined in one unit dose. In one embodiment, the naproxen sodium and the fexofenadine is in the form of a tablet, lozenge or chewing gum.

In one embodiment, the daily amount of ibuprofen is about 200 mg to about 800 mg. In one embodiment, the daily amount of aspirin is about 325 mg to about 1000 mg. In one embodiment, the daily amount of ketotifen is about 0.5 mg to about 2 mg. In one embodiment, the daily amount of desloratadine is about 5 mg to about 10 mg.

In one aspect, the present invention provides a pharmaceutical composition comprising a) a NSAID, and/or a salt thereof; and b) a co-agent. In one embodiment, the pharmaceutical composition is in the form of an orally-dissolving tablet or lozenge.

DETAILED DESCRIPTION OF THE INVENTION

In one embodiment, the present invention is directed to methods, and pharmaceutical compositions, to inhibit the symptoms associated with the common cold before the onset of such symptoms. The methods include the administration of particular pharmaceutical compositions.

In another embodiment, the present invention is directed to methods, and pharmaceutical compositions, to inhibit the symptoms associated with the common cold at the first appearance of at least one symptom of the common cold. The methods include the administration of particular pharmaceutical compositions.

Throughout this specification, quantities are defined by ranges, and by lower and upper boundaries of ranges. Each lower boundary can be combined with each upper boundary to define a range. The lower and upper boundaries should each be taken as a separate element.

The pharmaceutical composition comprises a) at least one non-steroidal anti-inflammatory drug ("NSAID"), and/or salts thereof, and b) a co-agent.

The NSAID of the present invention includes any NSAID. Examples of suitable NSAIDs include, but are not limited to, aspirin (i.e., acetylsalicylic acid); ibuprofen (i.e., isobutylphenylpropanoic acid); naproxen (i.e., 6-methoxy-α-methyl-2-naphthaleneacetic acid); diclofenac (i.e., 2-[(2,6-dichlorophenyl)-amino]benzene acetic acid); diflunisal (i.e., 2',4'-difluoro-4-hydroxybiphenyl-3-carboxylic acid); etodolac (i.e., (RS)-2-(1,8-diethyl-4,9-dihydro-3H-pyrano[3,4-b]indol-1-yl)acetic acid); indomethacin (i.e., 2-{1-[(4-chlorophenyl)-carbonyl]-5-methoxy-2-methyl-1H-indol-3-yl}acetic acid); ketoprofen (i.e., 3-benzoyl-α-methyl-benzeneacetic acid); ketorolac (i.e., 2-amino-2-(hydroxymethyl)-1,3-propanediol); meloxicam (i.e., 4-hydroxy-2-methyl-N-(5-methyl-2-thiazolyl)-2H-1,2-benzothiazine-3-carboxamide-1,1-dioxide); nabumetone (i.e., 4-(6-methoxy-2-naphthyl)-2-butanone); oxaprozin (i.e., 3-(4,5-diphenyl-1,3-oxazol-2-yl)propanoic acid); piroxicam (i.e., 4-hydroxy-2-methyl-N-2-pyridinyl-2H-1,2-benzothiazine-3-carboxamide 1,1-dioxide); salsalate (i.e., 2-(2-hydroxybenzoyl)-oxybenzoic acid); sulindac (i.e., {(1Z)-5-fluoro-2-methyl-1-[4-(methylsulfinyl)-benzylidene]-1H-indene-3-yl}acetic acid); and tolmetin (i.e., [1-methyl-5-(4-methylbenzoyl)-1H-pyrrol-2-yl]acetic acid).

Suitable co-agents include desloratadine (i.e., 8-chloro-6,11-dihydro-11-(4-piperidinylidene)-5H-benzo[5,6]cyclohepta[1,2-b]pyridine); fexofenadine (i.e., (±)-4-[1 hydroxy-4-[4-(hydroxydiphenylmethyl)-1-piperidinyl]-butyl]-α,α-dimethyl benzeneacetic acid); ketotifen, and salts thereof.

The NSAIDs and co-agents include all pharmaceutically acceptable versions of the NSAIDs and co-agents, including, for example, stereoisomers and/or any mixtures thereof, all pharmaceutically acceptable zwitterions and/or any mixtures thereof, all pharmaceutically acceptable polymorphic forms and/or any mixtures thereof, and all pharmaceutically acceptable complexes (including solvates) and/or any mixtures thereof.

Salts include all salts of NSAIDs and of co-agents which are pharmaceutically acceptable (i.e., non-toxic at therapeutically effective doses). And, salts include their racemates, enantiomers, or any mixtures thereof.

Particularly suitable salts of the NSAIDs comprise alkali-metal salts (e.g., sodium and/or potassium salts), alkaline earth metal salts (e.g., magnesium and/or calcium salts), aluminum salts, ammonium salts, salts of suitable organic bases (e.g., salts of alkylamines and/or -methyl-D-glutamine), salts of amino acids (e.g., salts of arginine and/or lysine). The NSAID salts also include all enantiomeric salts formed with pharmaceutically acceptable chiral acids and/or bases and/or any mixtures of enantiomers of such salts (e.g., (+) tartrates, (−) tartrates and/or any mixtures thereof including racemic mixtures). For example, a typical salt of an NSAID is naproxen sodium.

Examples of suitable salts of the co-agents include ketotifen fumarate and fexofenadine hydrochloride.

Symptoms of the common cold typically appear one to three days after exposure to a cold-causing virus. The symptoms of the common cold include, for example, substantial physical and mental fatigue, drowsiness, nausea, loss of appetite, cough, runny nose, nasal congestion, lung congestion, bronchial irritation, neuritis, neuralgia, sore throat, pain, aches (e.g., body aches), inflammation, sneezing, coughing, otitis, rhinitis, rhinorrhea, sinusitis, coryza, itchy and watery eyes, headache, low-grade fever, malaise, chills, muscle/joint pain, and the like.

The methods of the present invention comprise the administration of the pharmaceutical composition to a human, in need thereof, in an amount which is effective to inhibit the symptoms of the common cold.

In one embodiment, human subjects who are in need of the pharmaceutical compositions of the present invention are those who have a high risk of acquiring (i.e., contracting) the common cold. Examples of such subjects include those who work in close quarter settings (e.g., daycare centers, airplanes, restaurants, schools, physician offices), those who were near a person known to be infected (e.g., cohabitation), those who were under recent stress, and those who had recent sleep disturbances. In another embodiment, human subjects who are in need of the pharmaceutical compositions of the present invention are those who would like to ensure a minimization of symptoms should they acquire the common cold in a particular time period. For example, a subject may have an upcoming social or business event which would be compromised by the symptoms of the common cold (e.g., a wedding, an examination, a vacation).

In such embodiment, the pharmaceutical composition is administered to the human subject, in need thereof, before the onset of at least one symptom of the common cold. For example, administration is at most about one week before onset of a symptom, at most about four days before onset of a symptom, at most about three days before onset of a symptom, at least about two days before onset of a symptom, at least about one day before onset of a symptom, at least about 12 hours before onset of a symptom, at least about six hours before onset of a symptom, at least about three hours before onset of a symptom, at least about one hour before onset of a symptom, or right before the onset of a symptom. Typically, the pharmaceutical composition is administered on a substantially daily basis during such period. In one embodiment, the pharmaceutical composition is continued in a reduced amount (typically about half the initial amount) thereafter.

In a further embodiment, human subjects in need of the pharmaceutical compositions of the present invention are those who present with at least one initial sign of a symptom. Examples of initial signs are minor symptoms, including, for example, a slightly scratchy throat, slight headache, malaise. In this embodiment, the pharmaceutical composition is administered to the human subject at the initial sign of a symptom, or within about 12 hours of the initial sign of a symptom, or within about 24 hours of the initial sign of a symptom.

In the present specification, the term "inhibit" includes "reduce" and/or "prevent" and/or "shorten duration." That is, the method of the present invention is considered to be effective if it causes one or more of: a reduction/prevention of any symptom associated with the common cold and/or shortening of the duration of an episode of any such symptom.

Inhibition of symptoms can be assessed by comparing the magnitude and/or duration of at least one symptom in a subject at two different occasions, that is, i) when administered the pharmaceutical composition, and then the subject presents with the common cold; and ii) when not administered the pharmaceutical composition, and then the subject presents with the common cold. Inhibition of symptoms can also be assessed by comparing the magnitude and/or duration of at least one symptom in subjects exposed to the same virus; e.g., the subjects attend the same school classroom or cohabit in a family setting when exposed to the virus.

Typically, symptoms of the common cold are inhibited by at least about 10%, at least about 20%, at least about 30%, at least about 40%, at least about 50%, at least about 60%, at least about 70%, at least about 80%, at least about 90%, or at least about 100%.

For example, by the methods of the invention, inhibition of the symptoms of congestion and coughing were reduced by 70% and 90%, respectively; and muscle/joint pain, fever and sneezing were prevented.

It has unexpectedly been found that the components of the compositions of the present invention have a synergistic effect when inhibiting the symptoms of the common cold. For example, taking an NSAID on a daily basis is associated with adverse gastrointestinal effects (e.g., upset stomach, ulcers). However, when the NSAIDs of the present invention are taken in combination with the co-agents, they have surprisingly been found to decrease or avoid adverse gastrointestinal effects.

The actual preferred amounts of pharmaceutical composition in a specified case will vary according to the particular compositions formulated, the mode of application, the particular sites of application, and the subject being treated (e.g., age, gender, size, tolerance to drug, etc.).

Examples of typical daily amounts of NSAIDs to be administered in the methods of the present invention follows. The daily amounts can be administered in one dose, or in multiple doses, typically, two doses.

Naproxen from about 150 mg to about 900 mg: Examples of other lower boundaries of this range include about 220 mg, about 275 mg, about 320 mg and about 420 mg. Examples of other upper boundaries of this range include about 580 mg, about 680 mg, about 780 mg and about 880 mg. Other suitable amounts of naproxen include from about 110 mg to about 950 mg.

Ibuprofen from about 150 mg to about 900 mg: Examples of other lower boundaries of this range include about 200 mg, about 220 mg, about 320 mg and about 420 mg. Examples of other upper boundaries of this range include about 580 mg, about 680 mg, about 780 mg and about 800 mg. Other suitable amounts of ibuprofen include from about 100 mg to about 950 mg.

Aspirin from about 250 mg to about 1200 mg: Examples of other lower boundaries of this range include about 325 mg, about 450 mg, about 550 mg and about 650 mg. Examples of other upper boundaries of this range include about 750 mg, about 850 mg, about 950 mg, and about 1000 mg.

Examples of typical daily amounts of the co-agent to be administered in the methods of the present invention follows. The daily amounts can be administered in one dose, or in multiple doses, typically, two doses.

Fexofenadine from about 25 mg to about 200 mg: Examples of other lower boundaries of this range include about 60 mg, about 70 mg, about 80 mg and about 90 mg. Examples of other upper boundaries of this range include about 100 mg, about 120 mg, about 150 mg and about 180 mg. Ketotifen from about 0.5 mg to about 3 mg: Examples of other lower boundaries of this range include about 1 mg, about 1.5 mg and about 1.8 mg. Examples of other upper boundaries of this range include about 2 mg, about 2.5 mg and about 2.8 mg. Desloratadine from about 2 mg to about 40 mg: Examples of other lower boundaries of this range include about 5 mg, about 6 mg and about 7 mg. Examples of other upper boundaries of this range include about 8 mg, about 9 mg and about 10 mg; and about 20 mg, about 25 mg and 30 mg.

In one embodiment of the invention, the pharmaceutical composition of 220 mg naproxen and 60 mg fexofenadine is administered every twelve hours for at least two days starting once exposure to a cold virus is suspected.

In another embodiment of the invention, the pharmaceutical composition of 220 mg naproxen and 60 mg fexofenadine is administered every twelve hours for at least two days starting at the initial presentation of at least one symptom of the common cold.

The pharmaceutical composition can be administered by methods known in the art. For example, the pharmaceutical composition can be administered systemically. For the purposes of this specification, "systemic administration" means administration to a human by a method that causes the compositions to be absorbed into the bloodstream.

In one embodiment, the pharmaceutical compositions are administered orally by any method known in the art. For example, the compositions can be administered in the form of tablets, including, e.g., orally-dissolvable tablets, chewable tablets; capsules; lozenges; pills (e.g., pastilles, dragees); troches; elixirs; suspensions; syrups; wafers; chewing gum; strips; films (e.g., orally-dissolving thin films); soluble powders; effervescent compositions; and the like.

The NSAID (and/or salt thereof) and the co-agent (and/or and salts thereof) can be supplied in combination as one unit dose, or can be supplied individually, e.g., supplied in a package with a unit dose of NSAID and a unit dose of the co-agent.

Additionally, the pharmaceutical compositions can be administered enterally or parenterally, e.g., intravenously; intramuscularly; subcutaneously, as injectable solutions or suspensions; intraperitoneally; sublingually; or rectally (e.g., by suppositories). Administration can also be intranasally, in the form of, for example, an intranasal spray; or transdermally, in the form of, for example, a patch.

The pharmaceutical composition compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the pharmaceutically compositions can be employed, and the pH of the solutions can be suitably adjusted and buffered. For intravenous use, the total concentration of the solute(s) can be controlled in order to render the preparation isotonic.

A preferred embodiment of the invention is an orally dissolving tablet comprising an NSAID and a coagent with or without a taste masking ingredient, diluents, etc. Such tablet can be administered without water onto the tongue leading to immediate dissolution and is absorbed gastrointestinally or buccally. Orally dissolving tablets can be formulated by a number of techniques including compression and lyophilization, as would be known to a skilled artisan.

Another preferred embodiment of the invention is a lozenge or troche comprising an NSAID and a coagent with or without a taste masking ingredient, diluents, etc. Such lozenge/troche can be administered without water, and can slowly dissolve in the mouth, or can be swallowed or chewed. Such lozenges/troches can be formulated by compression, as would be known to a skilled artisan.

The pharmaceutical compositions of the present invention can further comprise one or more pharmaceutically acceptable additional ingredient(s) such as alum, stabilizers, buffers, coloring agents, flavoring agents, and the like. In some embodiments, orally administered pharmaceutical compositions can contain breathe neutralizers, e.g., peppermint or menthol scents.

The pharmaceutical composition may be administered by controlled release. Controlled release administration is a method of drug delivery to achieve a certain level of the drug over a particular period of time. The level typically is measured by plasma concentration. Methods for controlled release of drugs are well known in the art.

The pharmaceutical compositions can be formulated for controlled release. For example, in one embodiment, the composition can be a capsule containing beadlets, wherein some of the beadlets dissolve instantaneously and some of the beadlets dissolve at delayed times due to different types of beadlet coatings.

In one embodiment, the pharmaceutical composition comprises an active ingredient, wherein the active ingredient consists of: a) NSAID, and/or salt thereof, and b) a co-agent selected from the group consisting of: fexofenadine, ketotifen, desloratadine, salts thereof and combinations thereof.

In one embodiment, the pharmaceutical composition consists of: a) NSAID, and/or salt thereof, b) a co-agent selected from the group consisting of: fexofenadine, ketotifen, desloratadine, salts thereof, and combinations thereof; and c) at least one carrier and/or excipient.

In one embodiment, the pharmaceutical composition consists essentially of the active ingredients of: a) NSAID and/or salt thereof, and b) a co-agent selected from the group consisting of: fexofenadine, ketotifen, desloratadine, salts thereof and combinations thereof. That is, any other ingredients that may materially affect the basic and novel characteristics of the active ingredients of the invention are specifically excluded from the composition. Any ingredient which can potentially cause an undesirable effect/side effect, including, for example, an allergic response, may materially affect the basic and novel characteristics of the active ingredients of the invention.

The following are some examples of components which may materially affect the basic and novel characteristics of the active ingredients of the pharmaceutical compositions and may be excluded from certain embodiments of the present invention: cyclooxygenase-2-selective inhibitors (i.e., COX-2-selective inhibitors) or prodrugs thereof, an adrenergic agent, an anticholinergic agent, zinc (e.g., zinc acetate, zinc gluconate, zinc sulfate), pleconaril, a phosphodiesterase type 4 modulator, recombinant human uteroglobin, interleukin-9 antagonists; interleukin-8 antagonists (e.g., antibodies and peptides having IL-8 antagonist or IL-8 receptor antagonist activity); calcium glycerophosphate; sedating antihistamines; decongestants; ginsenoside and/or compounds of formula (I) or a salt or solvate thereof:

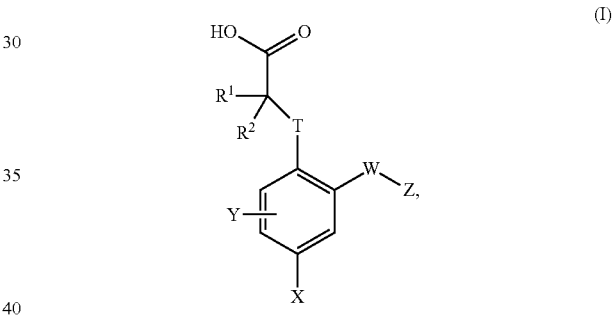

in which T is a bond, $S(O)_n$ (where n is 0, 1 or 2), $CR^1R^2$ or $NR^{13}$; W is O, $S(O)_n$ (where n is 0, 1 or 2), $NR^{13}$, $CR^1OR^2$ or $CR^1R^2$; X is hydrogen, halogen, cyano, nitro, $S(O)_nR^6$, $OR^{12}$ or $C_{1-6}$ alkyl which may be substituted by one or more halogen atoms; Y is selected from hydrogen, halogen, CN, nitro, $SO_2R^3$, $OR^4$, $SR^4$, $SOR^3$, $SO_2NR^4R^5$, $CONR^4R^5$, $NR^4R^5$, $NR^6SO_2R^3$, $NR^6CO_2R^6$, $NR^6COR^3$, $C_2$-$C_6$ alkenyl, $C_2$-$C_6$ alkynyl, $C_3$-$C_7$ cycloalkyl or $C_{1-6}$ alkyl, the latter four groups being optionally substituted by one or more substituents independently selected from halogen, $OR^6$ and $NR^6R^7$, $S(O)_nR^6$ where n is 0, 1 or 2; Z is aryl or heteroaryl, optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, $NR^6CONR^4R^5$, $NR^6SO_2NR^4R^5$, aryl, heteroaryl, $C_2$-$C_6$ alkenyl, $C_2$-$C_6$ alkynyl, $C_3$-$C_7$ cycloalkyl or $C_{1-6}$ alkyl, the latter four groups being optionally substituted by one or more substituents independently selected from halogen, $C_3$-$C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$; $R^1$ and $R^2$ independently represent a hydrogen atom, halogen, $C_2$-$C_6$ alkenyl, $C_2$-$C_6$ alkynyl, $C_3$-$C_7$ cycloalkyl or a $C_1$-$C_6$ alkyl group, the latter four groups being optionally substituted by one or more substituents independently selected from halogen, $C_3$-$C_7$ cycloalkyl, $NR^6R^7$, OR$^6$, S(O)$_n$R$^6$ (where n is 0, 1 or 2); or R$^1$ and R$^2$ together can form a 3-8 membered ring optionally containing one or more atoms selected from O, S, NR$^6$ and itself optionally substituted by one or more C$_1$-C$_3$ alkyl or halogen; R$^3$ represents C$_3$-C$_7$ cycloalkyl, C$_{1-6}$ alkyl, C$_2$-C$_6$ alkenyl or C$_2$-C$_6$ alkynyl all of which may be optionally substituted by one or more substituents independently selected from halogen, C$_3$-C$_7$ cycloalkyl, OR$^6$ and NR$^6$R$^7$, S(O)$_n$R$^6$ (where n=0, 1 or 2), CONR$^6$R$^7$, NR$^6$COR$^7$, SO$_2$NR$^6$R$^7$ and NR$^6$SO$_2$R$^7$; R$^4$ and R$^5$ independently represent hydrogen, C$_3$-C$_7$ cycloalkyl or C$_{1-6}$alkyl, the latter two groups being optionally substituted by one or more substituents independently selected from halogen, C$_3$-C$_7$ cycloalkyl, OR$^6$ and NR$^6$R$^7$, S(O)$_n$R$^6$ (where n=0, 1 or 2), CONR$^6$R$^7$, NR$^6$COR$^7$, SO$_2$NR$^6$R$^7$ and NR$^6$SO$_2$R$^7$; or R$^4$ and R$^5$ together with the nitrogen atom to which they are attached can form a 3-8 membered saturated heterocylic ring optionally containing one or more atoms selected from O, S(O)$_n$ (where n=0, 1 or 2), NR$^8$, and itself optionally substituted by halogen or C$_{1-3}$ alkyl; R$^6$ and R$^7$ independently represents a hydrogen atom or C$_1$-C$_6$ alkyl; R$^8$ is hydrogen, C$_{1-4}$ alkyl, —COC$_1$-C$_4$ alkyl, CO$_2$C$_1$-C$_4$ alkyl or CONR$^6$C$_1$-C$_4$ alkyl; R$^9$ represents aryl, heteroaryl, C$_3$-C$_7$ cycloalkyl or C$_{1-6}$ alkyl, the latter two groups may be optionally substituted by one or more substituents independently selected from halogen, C$_3$-C$_7$ cycloalkyl, aryl, heteroaryl OR$^6$ and NR$^6$R$^7$, S(O)$_n$R$^6$ (where n=0, 1 or 2), CONR$^6$R$^7$, NR$^6$COR$^7$, SO$_2$NR$^6$R$^7$ and NR$^6$SO$_2$R$^7$; R$^{10}$ and R$^{11}$ independently represent aryl or heteroaryl, hydrogen, C$_3$-C$_7$ cycloalkyl or C$_1$-C$_6$ alkyl, the latter two groups being optionally substituted by one or more substituents independently selected from halogen, C$_3$-C$_7$ cycloalkyl, aryl, heteroaryl, OR$^6$ and NR$^6$R$^7$, S(O)$_n$R$^6$ (where n=0, 1 or 2), CONR$^6$R$^7$, NR$^6$COR$^7$, SO$_2$NR$^6$R$^7$ and NR$^6$SO$_2$R$^7$; or R$^{10}$ and R$^{11}$ together with the nitrogen atom to which they are attached can form a 3-8 membered saturated heterocylic ring optionally containing one or more atoms selected from O, S(O)$_n$ (where n=0, 1 or 2), NR$^8$, and itself optionally substituted by halogen or C$_1$-C$_3$ alkyl; R$^{12}$ represents a hydrogen atom or C$_1$-C$_6$ alkyl which may be substituted by one or more halogen atoms, and R$^{13}$ represents a hydrogen atom, C$_{1-6}$ alkyl which may be substituted by one or more halogen atoms or C$_3$-C$_7$ cycloalkyl, SO$_2$R$^6$ or COC$_1$-C$_4$ alkyl, provided that when T is carbon or a bond, the substituent on group Z cannot be NR R$^{10}$R$^{11}$, where R$^{10}$R$^{11}$ are independently hydrogen, aryl, or alkyl, as defined in U.S. Pat. No. 8,022,248, which patent is incorporated by reference in its entirety.

The aforementioned ingredients may materially change the characteristics of the present pharmaceutical composition due to unwanted effects and/or potential allergic responses.

For example, decongestant and/or sedating effects are not desired in some embodiments of the invention.

Examples of unwanted potential effects of COX-2-selective inhibitors, or prodrugs thereof, include an increased risk in the incidence of myocardial infarctions. COX-2-selective inhibitors are compounds which selectively inhibit cyclooxygenase-2 over cyclooxygenase-1, and also include pharmaceutically acceptable salts of such compounds, and prodrugs of such compounds. A COX-2 selective inhibitor is any inhibitor for which the ratio of COX-1 IC$_{50}$ to COX-2 IC$_{50}$ is greater than 1. Examples of COX-2 selective inhibitors are found in US2004/0029864, which patent publication is incorporated herein by reference in its entirety.

Examples of unwanted potential effects of an adrenergic agent include angina, hypertension or hypotension, tachycardia, arrhythmias, nervousness, headache, tremor, dry mouth, muscle cramps, palpitations, nausea, dizziness, fatigue, malaise, insomnia, hypokalemia, hyperglycemia, and metabolic acidosis. Examples of unwanted potential effects of anticholinergic agent include dry mouth, blurred vision, dry eyes, constipation, urinary retention, dizziness, cognitive problems (confusion), heart rhythm disturbance. Examples of unwanted potential effects of pleconaril include headache, diarrhea, and nausea. Examples of unwanted potential effects of antibody/antibody fragments include allergic reactions, fever and vomiting. Examples of unwanted potential effects of phosphodiesterase type 4 modulators include nausea, vomiting, and related general gastrointestinal side effects. Examples of unwanted potential effects of ginsenoside include hormone-like effects (e.g., menstrual problems, breast pain, vaginal bleeding), insomnia, increased heart rate, blood pressure variations, headache, diarrhea, itching, rash, dizziness, mood changes. Examples of unwanted potential effects of zinc include nausea, vomiting, diarrhea, metallic taste, kidney and stomach damage. Examples of unwanted potential effects of calcium glycerophosphate include taste problems and incomplete or infrequent bowel movements.

EXAMPLES

The following examples demonstrate that common cold symptoms are inhibited when using the methods of the present invention. JMI-001 is 220 mg naproxen combined with 60 mg fexofenadine (marketed as EXULTA® by Sen-Jam Pharmaceutical LLC).

Example A

A middle-aged man (i.e., Subject A) was believed to have been exposed to the common cold while at a conference. Two days after returning home from the conference and for the subsequent 14 days, he suffered with symptoms associated with the common cold. On days 5-14, because his common cold symptoms were so severe Subject A took several over-the-counter products (i.e., a cough suppressant, a throat lozenge, a decongestant) for the treatment of symptoms associated with the common cold. On day 14, Subject A saw his primary care physician who diagnosed him with viral upper respiratory infection but prescribed antibiotics and steroids. On day 16, Subject A subjectively evaluated the magnitude of his past cold symptoms using a scale 0 to 10 (0=no symptom, 10=highest magnitude of symptom possible), as follows:

| | |
|---|---|
| runny nose | 0 |
| nasal congestion | 10 |
| sneezing | 0 |
| coughing | 10 |
| headache | 8 |
| fever | 2 |
| chills | 2 |
| muscle/joint pain | 8 |
| sore throat | 0 |

Example B

Subject B (i.e., the spouse of Subject A) believes she extracted the common cold from Subject A. The first sign of a symptom occurred 4 days after the return of Subject A to their home. Subject B administered to herself JMI-001 every 12 hours for 8 doses. She reports having cold symptoms for approximately 7 days and on day 10, she subjectively evaluated the magnitude of her past cold symptoms using a scale 0-10 (0=no symptom, 10=highest magnitude of symptom possible), as follows:

| | |
|---|---|
| runny nose | 4 |
| nasal congestion | 3 |
| sneezing | 1 |
| coughing | 1 |
| headache | 1 |
| fever | 0 |
| chills | 1 |
| muscle/joint pain | 0 |
| sore throat | 0 |

Example C

Subject C, an adult female, was living in a home with three family members all experiencing symptoms of the common cold. All family members' symptoms had started approximately 4 days earlier. Subject C complained of having one symptom which she believed to be the start of the common cold, and administered JMI-001 every 12 hours for 4 doses, then two subsequent doses, one on day 4, and one on day 5. On day 14, she retrospectively evaluated the magnitude of her past cold symptoms using a scale 0-10 (0=no symptom, 10=highest magnitude of symptom possible), as follows:

| | |
|---|---|
| runny nose | 2 |
| nasal congestion | 0 |
| sneezing | 0 |
| coughing | 0 |
| headache | 1 |
| fever | 0 |
| chills | 1 |
| muscle/joint pain | 1 |
| sore throat | 1 |

Example D

Subject D (i.e., the husband of Subject C) did not take JMI-001. He experienced cold symptoms for approximately 10 days and after his cold subsided, he subjectively evaluated the magnitude of his past cold symptoms using a scale 0-10 (0=no symptom, 10=highest magnitude of symptom possible), as follows:

| | |
|---|---|
| runny nose | 5 |
| nasal congestion | 7 |
| sneezing | 3 |
| coughing | 4 |
| headache | 3 |
| fever | 1 |
| chills | 1 |
| muscle/joint pain | 2 |
| sore throat | 3 |

Example E

A 22 yo male Subject E compares his experience at two different occasions 1) when he had a first sign of a common cold symptom and he did not take JMI-001, and 2) when he had a first sign of a common cold symptom and he self-administered JMI-001 every 12 hours for 6 doses. He subjectively evaluated the magnitude of his cold symptoms using a scale 0-10 (0=no symptom, 10=highest magnitude of symptom possible), as follows:

Common Cold without JMI-001 administration: Duration 7 days
Runny Nose=1
Nasal Congestion=5
Sneezing=3
Coughing=4
Headache=4
Fever=3
Chills=4
Muscle/joint pain=3
Sore throat=3
Common cold with JMI-001 administration: Duration 5 days
Runny Nose=0
Nasal Congestion=3
Sneezing=3
Coughing=2
Headache=2
Fever=0
Chills=0
Muscle/joint pain=2
Sore throat=1

Example F

A 57 yo female Subject F compares her experience at two different occasions 1) when she had a first sign of a common cold symptom and she did not take JMI-001, and 2) when she had a first sign of a common cold symptom and she self-administered JMI-001 every 12 hours for 6 doses. She subjectively evaluated the magnitude of her cold symptoms using a scale 0-10 (0=no symptom, 10=highest magnitude of symptom possible), as follows:

Common Cold without JMI-001 administered: Duration 8 days
Runny Nose=10
Nasal Congestion=10
Sneezing=2
Coughing=2
Headache=5
Fever=3
Chills=3
Muscle/joint pain=10
Sore throat=2
Common cold with JMI-001 administered: Duration 3 days
Runny Nose=2
Nasal Congestion=2
Sneezing=2
Coughing=2
Headache=0
Fever=0
Chills=0
Muscle/joint pain=2
Sore throat=0

Thus, while there have been described what are presently believed to be the preferred embodiments of the present invention, other and further embodiments, modifications, and improvements will be known to those skilled in the art, and it is intended to include all such further embodiments, modifications, and improvements as come within the true scope of the claims as set forth below.

The invention claimed is:

1. A method of inhibiting the symptoms associated with viral upper respiratory tract infection, consisting of:
 administering an effective amount of a pharmaceutical composition to a subject at risk of acquiring the viral upper respiratory tract infection, and before viral upper respiratory tract symptoms appear, wherein the active ingredients of the pharmaceutical composition consist of:
 a) a non-steroidal anti-inflammatory drug (NSAID), and/or a salt thereof; and
 b) a co-agent selected from the group consisting of: fexofenadine, ketotifen, desloratadine, salts thereof, and combinations thereof;
 wherein the pharmaceutical composition does not include a decongestant, and
 wherein the symptoms associated with the viral upper respiratory tract infection are inhibited.

2. The method of claim 1 wherein the NSAID is naproxen.

3. The method of claim 1 wherein the NSAID is naproxen sodium and the co-agent is fexofenadine.

4. The method of claim 3 wherein the amount of naproxen sodium is about 220 mg to about 880 mg, and the amount of fexofenadine is about 60 mg to about 180 mg.

5. The method of claim 3 wherein the naproxen sodium and the fexofenadine is in the form of a tablet, lozenge or chewing gum.

6. The method of claim 1 wherein the symptoms include congestion, coughing, fever, and/or muscle/joint pain.

7. The method of claim 1 wherein the viral upper respiratory tract infection is rhinovirus infection.

8. The method of claim 1 wherein the viral upper respiratory tract infection is acute viral rhinitis, nasopharyngitis, rhinopharyngitis, or acute coryza.

9. The method of claim 1, wherein the pharmaceutical composition comprises a pharmaceutical carrier or excipient.

10. A method of inhibiting the symptoms associated with viral upper respiratory tract infection, consisting of:
 administering to a subject an effective amount of a pharmaceutical composition prior to appearance of a viral upper respiratory tract infection symptom, wherein the active ingredients of the pharmaceutical composition consist of:
 a) about 220 mg to about 880 mg of naproxen sodium, and
 (b) about 60 mg to about 180 mg fexofenadine,
 wherein the pharmaceutical composition does not include a decongestant, and
 wherein the symptoms associated with the viral upper respiratory tract infection are inhibited.

11. The method of claim 10 wherein the viral upper respiratory tract infection is rhinovirus infection.

12. The method of claim 10 wherein the viral upper respiratory tract infection is acute viral rhinitis, nasopharyngitis, rhinopharyngitis, or acute coryza.

13. The method of claim 10, wherein the pharmaceutical composition is an orally dissolving tablet or lozenge.

14. The method of claim 10, wherein the pharmaceutical composition comprises a pharmaceutical carrier or excipient.

* * * * *